United States Patent
Starr

(10) Patent No.: US 11,684,391 B2
(45) Date of Patent: *Jun. 27, 2023

(54) SYSTEM, KIT AND APPARATUS FOR ATTACHMENT OF EXTERNAL FIXATORS FOR BONE REALIGNMENT

(71) Applicant: Board of Regents, The University of Texas System, Austin, TX (US)

(72) Inventor: Adam Starr, Dallas, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 399 days.

This patent is subject to a terminal disclaimer.

(21) Appl. No.: 16/549,428

(22) Filed: Aug. 23, 2019

(65) Prior Publication Data

US 2020/0022729 A1 Jan. 23, 2020

Related U.S. Application Data

(63) Continuation of application No. 13/898,084, filed on May 20, 2013, now Pat. No. 10,433,872, which is a (Continued)

(51) Int. Cl.
*A61B 17/64* (2006.01)
*A61B 17/62* (2006.01)
(Continued)

(52) U.S. Cl.
CPC ...... *A61B 17/6433* (2013.01); *A61B 17/0293* (2013.01); *A61B 17/62* (2013.01);
(Continued)

(58) Field of Classification Search
CPC ..... A61B 17/62; A61B 17/64; A61B 17/6408; A61B 17/6416; A61B 17/6425;
(Continued)

(56) References Cited

U.S. PATENT DOCUMENTS 3,572,326 A * 3/1971 Jensen ............... A61B 17/0293
600/233
4,006,740 A 2/1977 Volkov et al.
(Continued)

FOREIGN PATENT DOCUMENTS

EP 0247684 B1 3/1992
WO 2008034081 A2 3/2008

OTHER PUBLICATIONS

United States Patent and Trademark Office (ISA), International Search Report and Written Opinion for PCT/US2007/078534 dated Jul. 7, 2008, 7 pp.
(Continued)

*Primary Examiner* — Amy R Sipp
(74) *Attorney, Agent, or Firm* — Edwin S. Flores; Daniel J. Chalker; Chalker Flores, LLP

(57) ABSTRACT

The present invention includes a system, kit and apparatus to aid in the realignment of one or more bones of a patient. The present invention provides a substantially rigid orthopedic stabilization scaffold for attachment of one or more external fixators for the realignment of one or more bones of a patient. The orthopedic stabilization scaffold includes a first anchorable frame and a second anchorable frame that are removably attachable to an operating table and connected adjustably by one or more crossbars.

8 Claims, 4 Drawing Sheets

Related U.S. Application Data continuation of application No. 11/521,813, filed on Sep. 15, 2006, now Pat. No. 8,486,068.

(51) Int. Cl.
 *A61B 17/02*    (2006.01)
 *A61B 17/88*    (2006.01)
 *A61B 17/00*    (2006.01)

(52) U.S. Cl.
 CPC .......... *A61B 17/6408* (2013.01); *A61B 17/88* (2013.01); *A61B 2017/00911* (2013.01); *A61B 2017/00915* (2013.01); *Y10T 29/49826* (2015.01)

(58) Field of Classification Search
 CPC .............. A61B 17/6433; A61B 17/645; A61B 17/6458; A61B 17/6466; A61B 17/02; A61B 17/0206; A61B 17/0218; A61B 17/025; A61B 17/0293; A61B 2017/0256–0275
 See application file for complete search history.

(56) References Cited

U.S. PATENT DOCUMENTS

| | | | |
|---|---|---|---|
| 4,185,623 | A | 1/1980 | Volkov et al. |
| 4,355,631 | A | 10/1982 | LeVahn |
| 4,361,144 | A | 11/1982 | Slatis et al. |
| 4,531,514 | A | 7/1985 | McDonald et al. |
| 4,616,632 | A | 10/1986 | Wigoda |
| 4,762,122 | A | 8/1988 | Slocum |
| 4,815,455 | A | 3/1989 | Kim |
| 4,969,888 | A | 11/1990 | Scholten et al. |
| 5,108,404 | A | 4/1992 | Scholten et al. |
| 5,196,012 | A | 3/1993 | Malka |
| 5,275,598 | A | 1/1994 | Cook |
| 5,350,378 | A | 9/1994 | Cole et al. |
| 5,358,504 | A | 10/1994 | Paley et al. |
| 5,458,599 | A | 10/1995 | Adobati |
| 5,527,310 | A | 6/1996 | Cole et al. |
| 5,676,664 | A | 10/1997 | Allard et al. |
| 6,162,222 | A | 12/2000 | Poka et al. |
| 6,221,082 | B1 | 4/2001 | Marino et al. |
| 6,260,220 | B1 | 7/2001 | Lamb et al. |
| 6,634,043 | B2 | 10/2003 | Lamb et al. |
| 7,008,389 | B2 | 3/2006 | Krieg et al. |
| 7,615,051 | B2 | 11/2009 | Hamel |
| 8,486,068 | B2 | 7/2013 | Starr |
| 10,433,872 | B2 | 10/2019 | Starr |
| 2003/0009167 | A1 | 1/2003 | Wozencroft |
| 2004/0167518 | A1* | 8/2004 | Estrada, Jr. ............ A61B 17/62 606/56 |
| 2006/0064103 | A1 | 3/2006 | Matta |
| 2006/0217650 | A1* | 9/2006 | O'Gara ............... A61B 17/6433 602/19 |
| 2006/0272979 | A1 | 12/2006 | Lubbers et al. |
| 2008/0200987 | A1* | 8/2008 | Copf, Jr. ............ A61B 17/7077 606/301 |

OTHER PUBLICATIONS

Osi, PROfx Marketing Brochure (2003), 5 pp.
Borer, et al., "The Effect of Screening for Deep Vein Thrombosis on the Prevalence of Pulmonary Embolism in Patients with Fractures of the Pelvis or Acetabelum: A Review of 973 Patients," Journal of Orthopaedic Trauma (Feb. 2005), 19:92-95.
Eastridge, et al., "The Importance of Fracture Patterning in Guiding Therapeutic Decision-Making in Hypotensive Patients with Pelvic Ring Disruptions," Journal of Trauma (Sep. 2002), 53-446-450.
Griffin, et al., "Vertically Unstable Pelvic Fractures Fixed with Percutaneous Iliosacral Screws: Does Posterior Injury Predict Fixation Failure?" Journal of Orthopaedic Trauma (2003), 17-399-405.
Keating, et al., "Early Fixation of the Vertically Unstable Pelvis: The Role of Iliosacral Screw Fixation of the Posterior Lesion," Journal of Orthopaedic Trauma (Feb. 1999), 13:107-113.
Nork, et al., "Percutaneous Stabilization of U-Shaped Sacral Fractures Using Iliosacral Screws: Technique and Early Results," Journal of Orthopaedic Trauma (2001), 15:238-246.
Starr, et al., "Percutaneous Fixation of the Columns of the Acetabulum: A New Technique," Journal of Orthopaedic Trauma (Jan. 1998), 12:51-58.
Starr, et al., "Preliminary Results and Complications Following Limited Open Reduction and Percutaneous Screw Fixation of Displaced Fractures of the Acetabulum," Injury (2001), 32:45-50.
Starr, et al., "Pelvic Ring Disruptions: Prediction of Associated Injuries, Transfusion Requirement, Pelvic Arteriography, Complications and Mortality," Journal of Orthopaedic Trauma (2002), 16:553-561.
Starr, et al., "Percutaneous Screw Fixation of Fractures of the Iliac Wing and Fracture Dislocations of the Sacro-Iliac Joint (OTA types 61-B2.2 and 61-B2.3, or Young-Burgess "Lateral Compression Type II" Pelvic Fractures)," Journal of Orthopaedic Trauma (2002), 16:116-123.
Starr, A. J., "Immediate Management of Pelvic Fractures," Operative Techniques in Orthopaedics (2003), 13:73-78.

\* cited by examiner

SYSTEM, KIT AND APPARATUS FOR ATTACHMENT OF EXTERNAL FIXATORS FOR BONE REALIGNMENT

CROSS-REFERENCE TO RELATED APPLICATIONS

This application is a Continuation Application of U.S. patent application Ser. No. 13/898,084 filed May 20, 2013, which is a Continuation Application of U.S. patent application Ser. No. 11/521,813 filed Sep. 15, 2006, now U.S. Pat. No. 8,486,068 issued Jul. 16, 2013, the entire contents of each of which are incorporated herein by reference.

TECHNICAL FIELD OF THE INVENTION

The present invention relates in general to the field of skeletal fracture reduction and, more particularly, to an adjustable radiolucent scaffold to aid in the stabilization and reduction of pelvic ring fractures.

BACKGROUND OF THE INVENTION

Without limiting the scope of the invention, its background is described in connection with orthopedic fracture reduction and stabilization scaffolding as an example. Pelvic fractures are complex injuries with significant associated morbidity and mortality. Surgical management of pelvic fractures is challenging.

Generally, the pelvic ring consists of 2 innominate bones connected anteriorly at the symphysis pubis and posteriorly to the sacrum. The pelvic bones are held in position by strong ligaments that connect the sacrum and ilium; that connect the sacrum and ischium; that connect the 2 pubic bones at the symphysis pubis (a movable articular joint without a synovial membrane); and that connect the sacrum and coccyx. In addition to holding the pelvic bones into position, the ligaments stabilize the pelvis and assist and/or resist in movement, rotation, external rotation forces, sagittal plane rotational deformities and vertical shearing of the pelvis. In addition, several important muscle groups are about the pelvis to impart stability to the pelvic ring, e.g., muscles of the pelvic floor, the levator ani muscle, the piriformis muscle and the coccygeus muscles.

Pelvic fractures are generally the result of severe trauma and blunt impacts on the pelvic girdle, which occur most often, for example, as a result of traffic accidents or falls. Patients who sustain pelvic ring disruptions are at risk for a myriad of acute and long term complications, such as exsanguinating hemorrhage, neurologic dysfunction, sexual dysfunction, leg length discrepancy, chronic pain, thromboembolic disease, chronic low back pain, limp and poor functional outcome. As such, patients must be transported to trauma centers for immediate surgical intervention as pelvic fractures are often accompanied by massive blood loss and internal bleeding that may result in death. In addition to the pelvic fracture, many patients present associated primary organ system injuries. Therefore, it is necessary to stabilize a fractured pelvis to reduce further bleeding and injury. Recent advances in treatment of these difficult injuries include the use of percutaneous methods of pelvic fracture stabilization.

Treatments require the fractured pelvic bones to be physically moved and aligned. The ligaments and muscles of the pelvis resist the movement and alignment of the pelvic bones. External fixation devices may be attached to the fractured bones and aid in the alignment and may be used to hold them in position until the patient is stable enough to undergo internal fixation surgical procedures. Once aligned, internal fixation is then used to provide stabilization for the pelvic ring fractures as the bones heal.

Currently, the technique of percutaneous screw fixation of pelvic ring disruptions involves the use of instruments placed against or into the bone through small incisions, guided by fluoroscopy. These instruments are used to re-align fractured bones while definitive stabilization is obtained using percutaneously placed cannulated screws. Successful percutaneous stabilization requires that the surgeons achieve and maintain an acceptable reduction, or alignment, of the injured bone while a screw is passed across the fracture. In most cases, manual traction on the leg is used to achieve fracture reduction. In many cases, metal surgical instruments are introduced through small stab incisions in order to push or pull the bone, to improve alignment. In all cases, fracture reduction is achieved through use of manual pressure by the surgeon's arms, or by traction applied through pins placed into the patient's bones. The pressure required to correct the fracture deformity is often substantial, since deforming forces acting on the fracture include major muscle groups about the patient's hip, lower abdomen and back.

While the surgeon or surgical assistant holds the reduction, another surgeon must accurately place a guide wire over which a cannulated screw will pass. Errant wire or screw placement can injure surrounding nerves, vessels or viscera. Placement of the guide wire and screw rely upon multi-planar fluoroscopic imaging to ensure accuracy. Thus, the surgical team includes of one or more surgeons focused on achieving and holding a perfect reduction, one surgeon focused on accurate, rapid placement of a guide wire and screw, and a skilled radiology technician moving a fluoroscope into multiple positions to ensure reduction is perfect and screw placement is accurate.

Traditional skeletal traction using a metal pin in the tibia or femur is sometimes used to improve alignment of pelvic fractures. Some currently marketed "fracture tables" are designed for this type of use. However, uni-planar longitudinal traction on the leg is often not sufficient to achieve perfect reduction of the fracture. Most pelvic fractures are not displaced in a single plane in line with the leg. Longitudinal traction may offer gross corrections of some displacements, but in most cases, multi-planar corrections are necessary. And since fracture tables do not allow the intact portions of the pelvis to be anchored into place, the pull of traction often results in an unacceptable tilt of the pelvis.

The foregoing problems have been recognized for many years and while numerous solutions have been proposed, none of them adequately address all of the problems in a single device, e.g., skeletal traction to improve alignment of pelvic fractures.

SUMMARY OF THE INVENTION

The present inventors recognized a need for radiolucent system and device that could be used to aid in the placement of bone pins at a variety of planes and positions to enable the multi-planar alignment of fractured bones, while holding the fractured bones firmly in place to minimize blood loss, lessen soft tissue dissection, and decrease the risk of wound complications after surgery.

The present invention is a pelvic reduction system to apply non-powered skeletal traction to the fractured pelvis during surgery in order to improve alignment of the bone and to facilitate fracture stabilization. The system consists of two semi-circular rings made of a radiolucent material, e.g., carbon fiber. The two rings are clamped securely to a radiolucent operating table and crossbars of carbon fiber then link the two rings to form a rigid "box" or "cage" over the patient's lower abdomen and pelvis to form the anchoring point for reduction instruments. The present invention allows the surgeon to apply traction in several planes to correct fracture deformity and then hold the correction until definitive fixation with screws or plates can be obtained.

The present invention provides a substantially rigid orthopedic stabilization scaffold for attachment of one or more external fixators for the realignment of one or more bones of a patient. The orthopedic stabilization scaffold includes a first and a second anchorable frames that are removably attachable to an operating table and connected adjustably by one or more crossbars.

The present invention provides a method of treating a patient using an orthopedic fracture reduction scaffold by connecting one or more external fixators to one or more bones and an orthopedic fracture reduction scaffold. The orthopedic fracture reduction scaffold includes a first and a second anchorable frame connected adjustably to an operating table and connected by one or more crossbars. The orthopedic fracture reduction scaffold forms a substantially rigid scaffold for attachment of one or more external fixators to realign the one or more bones of a patient. The one or more bones can then be aligned and subsequently stabilized by attaching one or more orthopaedic implants, screws, plates, bolts or a combination thereof. The aligning of the one or more bones may include adding, withdrawing, pushing, pulling, moving, or shifting the one or more external fixators to position, align and hold the bones.

In addition, the present invention provides a method of assembling an orthopedic fracture reduction scaffold on an operating table. A first anchorable frame and a second anchorable frame are attached to an operating table and connected by one or more crossbars. This forms a substantially rigid orthopedic fracture reduction scaffold for the attachment of one or more external fixators to aid in the realignment of one or more bones of a patient.

The present invention includes an orthopedic fracture stabilization scaffold kit. The kit includes a first anchorable frame adapted to fit an operating table, a second anchorable frame adapted to fit the operating table and one or more crossbars. The crossbars are adapted to connect removably to the first anchorable frame and the second anchorable frame to form a substantially rigid orthopedic fracture stabilization scaffold. The substantially rigid orthopedic fracture stabilization scaffold can then be used for attachment of one or more external fixators for the realignment of one or more bones of a patient.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The terminology used and specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention provides a substantially rigid orthopedic stabilization scaffold for attachment of one or more external fixators for the realignment of one or more bones of a patient. The orthopedic stabilization scaffold includes first and second anchorable frames that are removably attachable to an operating table and connected adjustably by one or more crossbars.

Generally, the orthopedic stabilization scaffold is constructed from or made with radiolucent materials. For example, the first anchorable frame, the second anchorable frame and/or the one or more crossbars may be constructed using carbon fiber or carbon composite; however, composites, plastics, polymers, Kevlar, nylons, resins (e.g., polyether imide) may also be used. Although, the orthopedic stabilization scaffold is designed to be radiolucent, other embodiments may have no need to be radiolucent and may be constructed from metals or alloys, e.g., stainless steel, steel, iron, titanium or combinations thereof. Similarly, some applications partially radiolucent and include segments or areas that are constructed from radiolucent materials and areas constructed from radio-opaque materials. For example, in some embodiments, portions of the first anchorable frame and the second anchorable frame may be made from radiolucent materials, while the one or more crossbars are made in part or entirely from radio-opaque materials. Alternatively, segments of the first anchorable frame and/or the second anchorable frame may be made from radiolucent materials, while the other portions may be made from a radio-opaque material.

Figure 1:
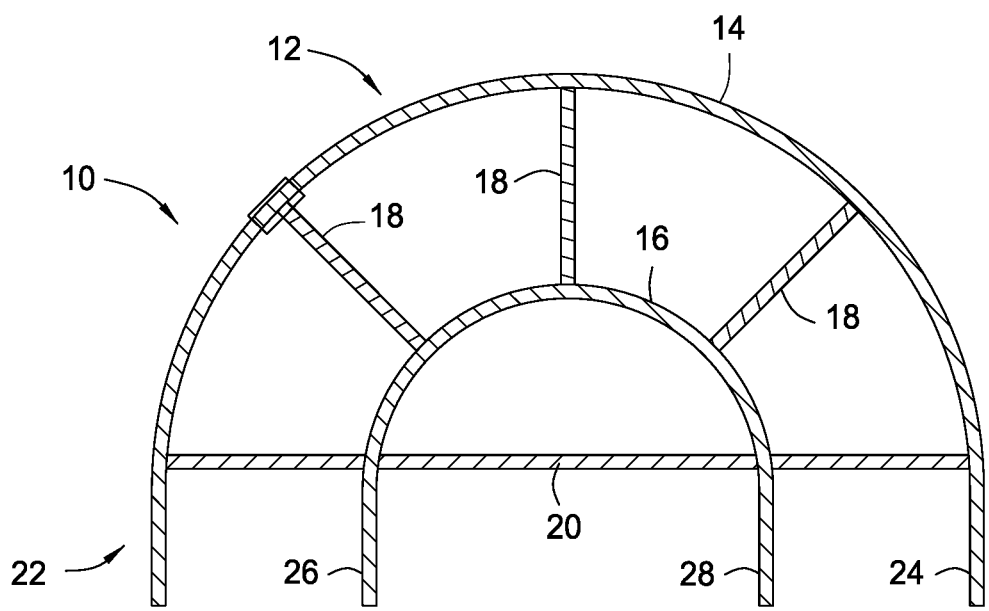
FIG. 1 is a side view of a portion of the one embodiment of the present invention.

FIG. 1 is a side view of a portion of the one embodiment of the present invention. The orthopedic stabilization scaffold 10 includes a first anchorable frame 12. The first anchorable frame 12 has a first rail 14 and a second rail 16 that are curved in concentric arcs and are connected to each other by connecting rails 18. The number and position of connecting rails 18 may be varied as necessary. A bottom rail 20 connects the first outer end 22 and second outer end 24 of the first rail 14 and the first inner end 26 and second inner end 28 of the second rail 16. The first outer end 22 is positioned about 9 inches from the first inner end 26 along the bottom rail 20. The first inner end 26 is positioned about 18 inches along the bottom rail 20 from the second inner end 28. The second inner end 28 is positioned about 9 inches along the bottom rail 20 from the second outer end 24. The first outer end 22 is about 36 inches from the second outer end 24. The first outer end 22, the second outer end 24, the first inner end 26 and the second inner end 28 extend (e.g., between about 2 and 8 inches and commonly about 6 inches) beyond the bottom rail 20 so that it can be secured to the operating table (not pictured). The connecting rails 18 are 18 inches long and connect the first rail 14 and the second rail 16. The distance from the bottom rail 20 to the top of the first rail 14 may be any distance dictated by the specific application, e.g., between about 6 and 24 inches and commonly 16 inches. The dimensions are exemplar in nature and the skilled artisan will know that the lengths and distances may be altered as necessary for the particular application. For example, the connecting rails 18 may be between 6 and 24 inches long. Furthermore, distance between the first outer end 22, the second outer end 24, the first inner end 26 and the second inner end 28 may be between 6 and 24 inches.

Figure 2:
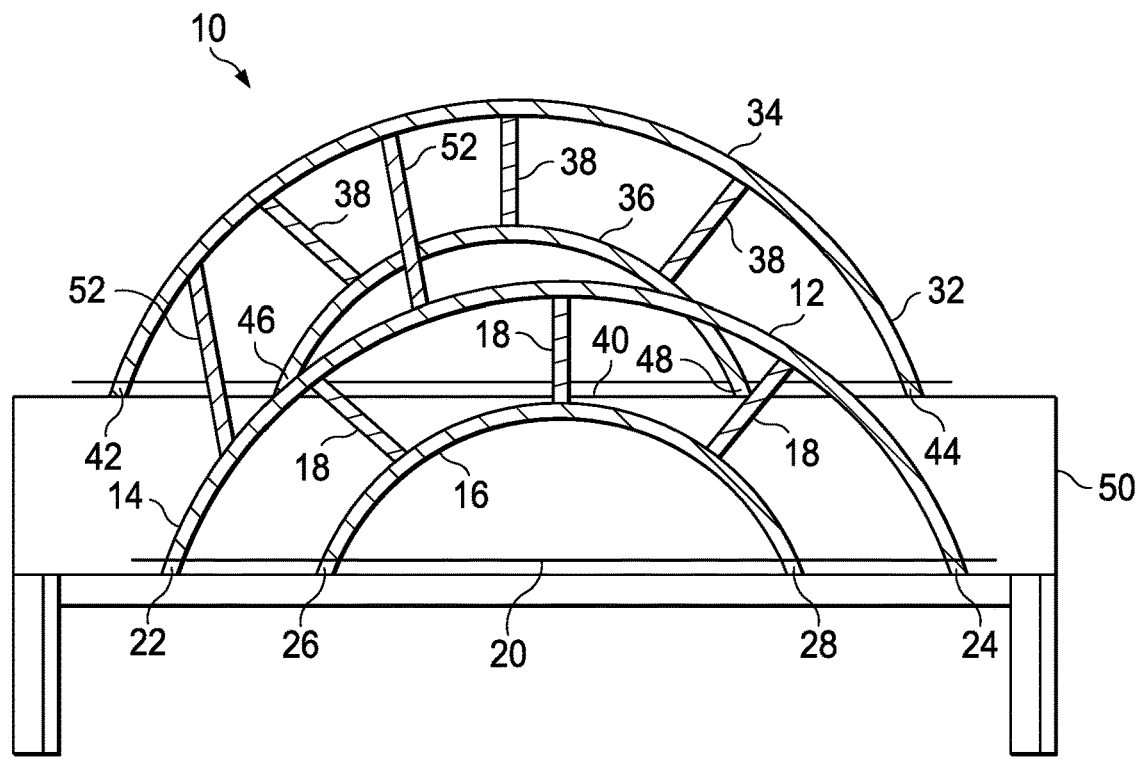
FIG. 2 is an isometric view of one embodiment of the present invention.

FIG. 2 is an isometric view of one embodiment of the present invention. The orthopedic stabilization scaffold 10 includes a first anchorable frame 12 and a second anchorable frame 32. The first anchorable frame 12 has a first rail 14 and a second rail 16 that are curved in concentric arcs and are connected to each other by connecting rails 18. The number and position of connecting rails 18 may be varied as necessary. A bottom rail 20 connects the first outer end 22 and second outer end 24 of the first rail 14 and the first inner end 26 and second inner end 28 of the second rail 16. The first outer end 22, the second outer end 24, the first inner end 26 and the second inner end 28 extend beyond the bottom rail 20. The second anchorable frame 32 has a first rail 34 and a second rail 36 that are curved in concentric arcs and are connected to each other by connecting rails 38. The number and position of connecting rails 38 may be varied as necessary. A bottom rail 40 connects the first outer end 42 and second outer end 44 of the first rail 34 and the first inner end 46 and second inner end 48 of the second rail 36. The first outer end 42 is positioned about 9 inches from the first inner end 46 along the bottom rail 40. The first inner end 46 is positioned about 18 inches along the bottom rail 40 from the second inner end 48. The second inner end 48 is positioned about 9 inches along the bottom rail 40 from the second outer end 44. The first outer end 42 is about 36 inches from the second outer end 44. The first outer end, the second outer end 44, the first inner end 46 and the second inner end 48 extend beyond the bottom rail 40. The first outer end 22 and 42, the second outer end 24 and 44, the first inner end 26 and 46 and the second inner end 28 and 48 are secured to opposite sides of the operating table 50. The first anchorable frame 12 and the second anchorable frame 32 are connected by crossbars 52

Generally, the substantially rigid orthopedic stabilization scaffold 10 includes a first anchorable frame 12 and a second anchorable frame 32 that are substantially perpendicular to the surface of the operating table 50 and substantially parallel to each other. Other embodiments may include a first anchorable frame 12 and a second anchorable frame 32 that are independently positioned at angles more or less than perpendicular relative to the operating table. The exact angle of the first anchorable frame 12 and the second anchorable frame 32 may be between about 30 degrees and about 150 degrees depending on the particular application and procedure.

Each crossbar is positioned generally perpendicular relative to the first anchorable frame 12 and the second anchorable frame; however, each crossbar may be positioned at any angle between about 20 degrees and about 160 degrees depending on the particular application and procedure relative to the first anchorable frame 12 and the second anchorable frame 32 to form a substantially rigid orthopedic stabilization scaffold. The general cross sectional shape of the crossbars 52 are circular; however, any cross sectional shape may be used, e.g., a triangle, an oval, a circle, a semi-circle, a rectangle, a polygon, a free form shape. In addition, the cross sectional shape may change as a function of the length of the crossbar 52. The number of crossbars 52 necessary to form a substantially rigid orthopedic stabilization scaffold 10 will depend on particular application. In addition, crossbars 52 can be added to the scaffold 10 to allow the connection of one or more external fixators, extensions, rods or clamps as necessary.

The shape of the first anchorable frame 12 and the second anchorable frame 32 may independently be an arc; however, other shapes may be used limited only by the particular need of the application. For example, the first anchorable frame 12 and/or the second anchorable frame 32 may be in the shape of a portion of an oval, a semi-circle, a portion of a rectangular, a free form shape or a combination thereof and may have a rounded shape, a pointed shape, a two-centered shape, a double curve or be in the shape of an upper arc and a lower arc, a triangle, an acute-angle triangles, a flattened circle or elliptical; and so forth. Furthermore, it is not necessary that the first anchorable frame 12 and the second anchorable frame 32 have the same shape only that crossbars 52 be connectable to the first anchorable frame 12 and the second anchorable frame 32, e.g., the first anchorable frame 12 may have an elliptical shape connecting by numerous crossbars 52 to a polygonal second anchorable frame.

Figure 3:
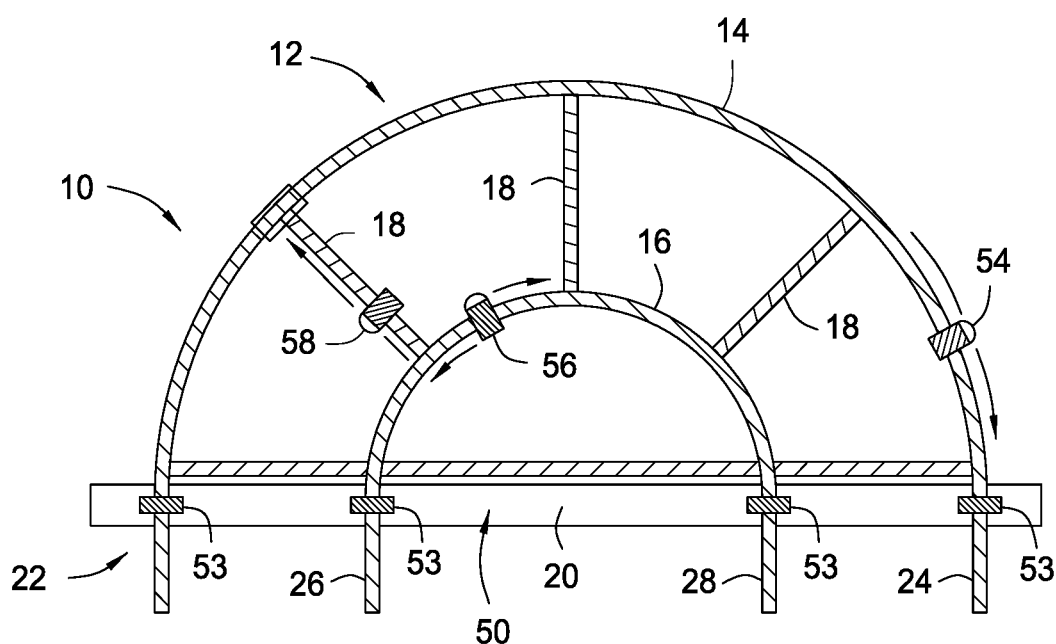
FIG. 3 is images of the rails of the present invention.

FIG. 3 is a side view of a portion of one embodiment of the present invention. The orthopedic stabilization scaffold 10 includes a first anchorable frame 12. The first anchorable frame 12 has a first rail 14 and a second rail 16 that are curved in concentric arcs and are connected to each other by connecting rails 18. The number and position of connecting rails 18 may be varied as necessary. A bottom rail 20 connects the first outer end 22 and second outer end 24 of the first rail 14 and the first inner end 26 and second inner end 28 of the second rail 16. The first outer end 22 is positioned about 9 inches from the first inner end 26 along the bottom rail 20. The first inner end 26 is positioned about 18 inches along the bottom rail 20 from the second inner end 28. The second inner end 28 is positioned about 9 inches along the bottom rail 20 from the second outer end 24. The first outer end 22, the second outer end 24, the first inner end 26 and the second inner end 28 extend beyond the bottom rail 20 so that it can be secured to the operating table 50 using mounts 53. A clamp 54 can be connected to the first rail 14 of the first anchorable frame 12, to the second rail 16 (e.g., clamp 56) and/or connecting rails 18 (e.g., clamp 58). The clamps 54, 56, 58 may be adjusted as needed.

Figure 4A:
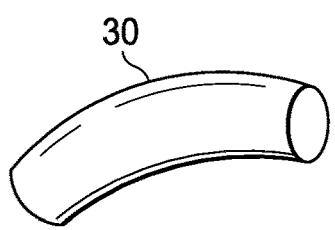
FIGS. 4a and 4b are a side view of a portion of the one embodiment of the present invention.
Figure 4B:
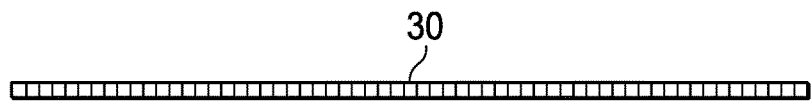
Figure 4B:
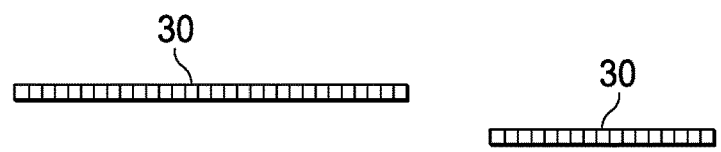

FIGS. 4a and 4b are images of the rails of the present invention. FIG. 4a is an isometric view of one of the rails 30 used in the present invention. The rail 30 may be of any diameter necessary, e.g., between about 3 mm and 20 mm and commonly 11 mm. FIG. 4b is a side view of one of the rails 30 of the present invention. The rail 30 may be of any length necessary, e.g., between about 6 inches and 36 inches and commonly 6, 12, 18, 20, 24, 30 and 36 inches.

Figure 5A:
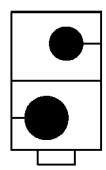
FIGS. 5a and 5b are clamps used with the present invention.
Figure 5B:
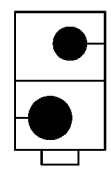

FIGS. 5a and 5b are clamps used with the present invention. Common clamps include bar to bar clamps FIG.

5a used to connect bars and pin to bar clamps as in FIG. 5b used to connect pins and bars. External fixators may be attached to the substantially rigid orthopedic stabilization scaffold 10 (not shown) at the first anchorable frame, the second anchorable frame, the one or more crossbars 52 (not shown) or a combination thereof as necessary for the fracture reduction and fixation. The external fixators are common in the art and well known to the skilled artisan.

Figure 6A:
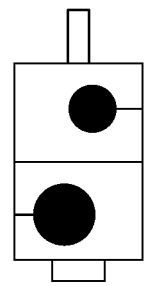
FIGS. 6a, 6b and 6c are images of clamps that may be used with the present invention.
Figure 6B:
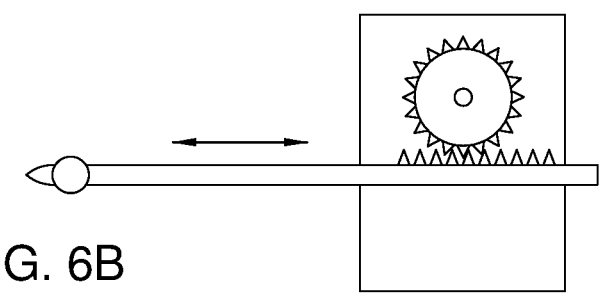
Figure 6C:
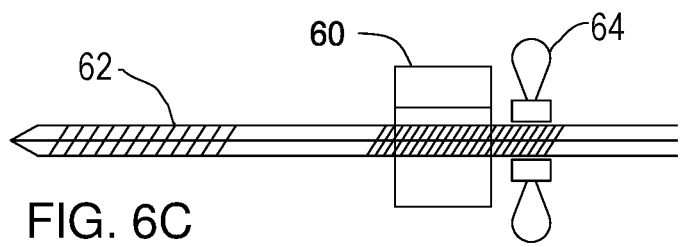

In addition, specialized clamps as seen in FIGS. 6a, 6b and 6c may be used with the present invention. FIG. 6a is a push-pull clamp that is used with a push or pull tool. FIG. 6b is a mechanical clamp that uses a gear and sprocket mechanism to push or pull a tool. FIG. 6c is a clamp 60 having a pin 62 that passes through the clamp 60 and a wing nut 64 to limit the movement of the pin 62.

Figure 7A:
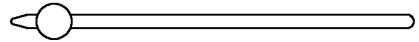
FIGS. 7a, 7b, 7c and 7d are images of tools that may be used with the present invention.
Figure 7B:
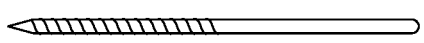
Figure 7C:
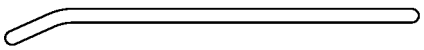
Figure 7D:

FIGS. 7a, 7b, 7c and 7d are images of tools that may be used with the present invention. FIG. 7a is an image of a ball spike, FIG. 7b is an image of a screw pin, FIG. 7c is an image of a jokevl and FIG. 7d is an image of a bone hook.

Generally, an external fixator includes a clamp, an adaptor, a pin or combination thereof. Examples of an external fixator include distractor single hole, distractor double hole, distractor open hole, spanner, k-wire, uniaxial hinge joint, biaxial hinge joint, link joints, straight rod (knurled), z-shaped rods, l-shaped rod (knurled), threaded rod, tubular rod, ordinary telescopic rods, graduated telescopic rods, compression distraction device, repofix device, single pin clamp, double pin clamp, open single pin clamp, twin adjustable clamp straight or curved, transverse clamp, tube to tube clamp, small connecting clamp, front threaded pins, front threaded pins (shanz screws), front threaded pins (blunt tip), cancellous front threaded pins, posts, hinges and combinations thereof. Specific external fixators include an adaptor, a clamp, a pin, a traction pin device, a ball-spike pusher device, an extension and other surgical devices used in fracture reduction. The orthopedic stabilization scaffold 10 can be used to anchor one or more percutaneous fracture reduction instruments.

Figure 8:
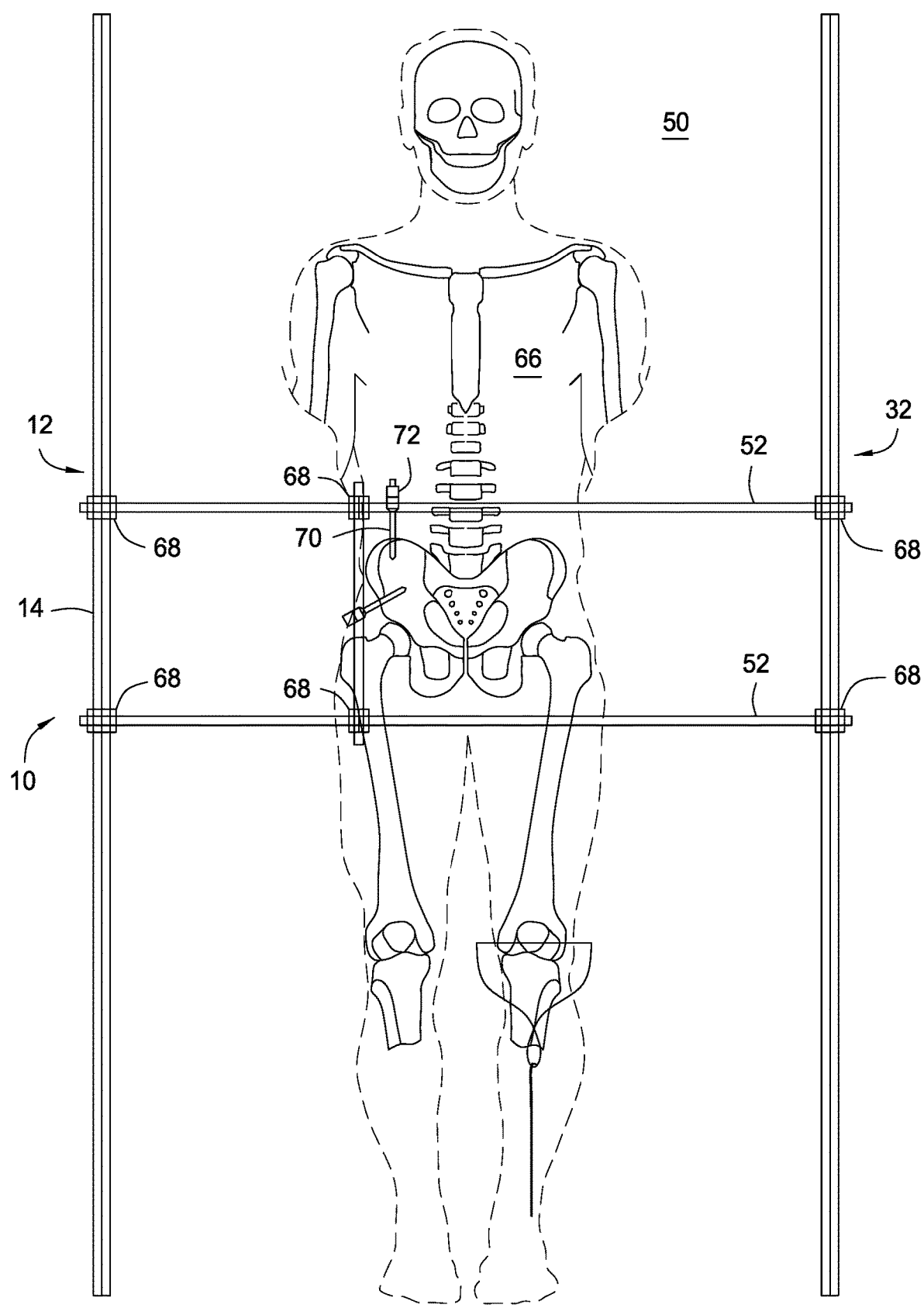
FIG. 8 is an image of the present invention in operation.

FIG. 8 is an illustration of the top view of the present invention in operation. The orthopedic stabilization scaffold 10 is positioned about patient 66. The orthopedic stabilization scaffold 10 includes a first anchorable frame 12 and a second anchorable frame 32. The first anchorable frame 12 has a first rail 14 and a second rail (not shown) that are curved in concentric arcs and are connected to each other by connecting rails (not shown). Similarly, the second anchorable frame 32 has a first rail 34 and a second rail (not shown) that are curved in concentric arcs and are connected to each other by connecting rails (not shown). A bottom rail (not shown) is connects to each of the first anchorable frame 12 and the second anchorable frame 32 to secured them to opposite sides of the operating table 50. The first anchorable frame 12 and the second anchorable frame 32 are connected by crossbars 52 using bar-to-bar clamps 68. Pins 70 are inserted into the patient 66 and connected using the pin to bar clamp 72.

Imaging devices may be used in conjunction with the present invention to aid in the alignment of bones or portions of bones and in positioning the one or more external fixators or a combination thereof. The skilled artisan will recognize the type of imaging devices that may be used and include multi-planar fluoroscopic imaging devices, x-ray imaging devices and the like.

The present invention provides that traction pins, ball-spike pushers or other surgical instruments can used, as they are used currently, to achieve fracture reduction. For example, these instruments are placed against the bone or into it using small stab incisions. Placement is guided by multi-planar fluoroscopic imaging, as is currently done. Manual pressure will be used to reduce the fracture fragments. Once bone alignment is achieved, these instruments can then be clamped to the present invention using commercially available external fixator system clamps, and anchored in position. Small corrections in alignment can be performed by withdrawing or pushing on threaded pins. Then, percutaneous fracture stabilization using standard orthopaedic implants can proceed.

The orthopedic fracture reduction scaffold of the present invention may be used to aid in positioning a variety of bones including the pelvis, the spine, the ribs, the femur, fibula, tibia, humerus, radius, ulna and so forth. In addition to humans, the orthopedic fracture reduction scaffold may be used to position bones of a variety of animals, e.g., horses, cows, birds, dogs, cats and so forth.

It is contemplated that any embodiment discussed in this specification can be implemented with respect to any method, kit, apparatus or system of the invention, and vice versa.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of treating a patient using an orthopedic fracture reduction scaffold comprising the steps of:
    anchoring a first anchorable frame and a second anchorable frame to an operating table, the operating table comprising
        a first side opposite a second side, wherein the first side is parallel to a patient's first arm and the second side is parallel to a patient's second arm,
        a head side connecting perpendicularly the first side and the second side at a head end, wherein a patient's head is positioned at the head end, and
        a foot side connecting perpendicularly the first side and the second side at a foot end, wherein a patient's feet are positioned at the foot end;
    wherein the first anchorable frame comprises at least one first arched rail and a first plurality of connecting rails, wherein the first plurality of connecting rails is circumferentially distributed along a radial direction, wherein the at least one first arched rail comprises a first attachment point and a second attachment point; wherein the first attachment point is removably attachable to a first location on the first side of the operating table and the second attachment point is removably attachable to a second location on the first side of the operating table;
    wherein the second anchorable frame comprises at least one second arched rail and a second plurality of connecting rails, wherein the second plurality of connecting rails is circumferentially distributed along a radial direction, wherein the at least one second arched rail comprises a first attachment point and a second attachment point; wherein the first attachment point of the second anchorable frame is removably attachable to a first location on the second side of the operating table and the second attachment point of the second anchorable frame is removably attachable to a second location on the second side of the operating table;
    connecting one or more crossbars to the first anchorable frame and the second anchorable frame to form a substantially rigid orthopedic fracture reduction scaffold for attachment of one or more external fixators to aid in the realignment of one or more bones of a patient, wherein the one or more bones are selected from a pelvis, femur, fibula, tibia, humerus, radius, or ulna;
    connecting one or more external fixators to the one or more bones and an orthopedic fracture reduction scaffold comprising the first and the second anchorable frame connected adjustably to the operating table and connected by the one or more crossbars to form the substantially rigid orthopedic fracture reduction scaffold for attachment of the one or more external fixators to realign the one or more bones of the patient; and
    aligning the one or more bones, wherein the one or more bones aligned are selected from the pelvis, femur, fibula, tibia, humerus, radius, or ulna.

2. The method of claim 1, further comprising stabilizing the one or more bones by attaching one or more orthopedic implants, screws, plates, bolts or a combination thereof.

3. The method of claim 1, wherein the step of aligning the one or more bones comprise adding, withdrawing, pushing, pulling, moving, or shifting the one or more external fixators.

4. The method of claim 1, wherein the orthopedic fracture reduction scaffold comprises a radiolucent material selected from carbon fiber, aluminum, an alloy, a composite, plastic, polymer, Kevlar, nylon, polyether imide resin and combinations thereof.

5. The method of claim 1, wherein the first anchorable frame and the second anchorable frame independently have a shape selected from a polygon, an oval, a semi-circle, a rectangle, a free form shape or a combination thereof; or wherein the first anchorable frame, the second anchorable frame or both the first and the second anchorable frame are substantially perpendicular to a surface of the operating table.

6. The method of claim 1, further comprising attaching one or more percutaneous fracture reduction instruments to the orthopedic fracture reduction scaffold.

7. The method of claim 1, wherein the one or more external fixators comprise a clamp, a screw, an adaptor, a pin a traction pin device, a ball-spike pusher device, an extension or other surgical device used to achieve fracture reduction.

8. The method of claim 1, further comprising using a multi-planar fluoroscopic imaging device to position the one or more external fixators for alignment of the one or more bones or a combination thereof.

* * * * *